US00PP15008P2

(12) United States Plant Patent
Utecht

(10) Patent No.: US PP15,008 P2
(45) Date of Patent: Jul. 13, 2004

(54) GERANIUM PLANT NAMED 'FISROMON'

(50) Latin Name: *Pelargonium zonale*
Varietal Denomination: Fisromon

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/715,536

(22) Filed: Nov. 19, 2003

(30) Foreign Application Priority Data

Dec. 23, 2002 (CA) ..... PBR 02-3403

(51) Int. Cl.[7] ..... A01H 5/00

(52) U.S. Cl. ..... Plt./327

(58) Field of Search ..... Plt./327, 328

*Primary Examiner*—Kent Bell
(74) *Attorney, Agent, or Firm*—Foley & Lardner LLP

(57) ABSTRACT

A new and distinct cultivar of geranium plant named 'Fisromon', particularly characterized by the combined features of salmon-pink with narrow white margin, semi-double flowers, big inflorescences well above the foliage, deep green foliage with strong zonation, medium to tall plant habit, and about medium begin of flowering.

1 Drawing Sheet

Genus and species of the invention: Hybrid *Pelargonium zonale* L'Héritier
Variety denomination: 'Fisromon'.

BACKGROUND OF THE INVENTION

The present invention comprises a new and distinct cultivar of geranium, botanically known as *Pelargonium zonale,* and hereinafter referred to by the cultivar name 'Fisromon'.

'Fisromon' is a product of a planned breeding program which had the objective of creating new zonal geranium cultivars with salmon flower color, relatively vigorous, but well-branched growth habit, and good outdoor performance.

'Fisromon' originated from a hybridization made by the inventor, Angelika Utecht, in a controlled breeding program in Hillscheid, Germany, in 1998. The female parent was an unpatented hybrid seedling, No. 95-30-5, having red single-type flowers, medium green foliage, with strong zonation, and medium sized plant habit, and derived from crosses between the commercial varieties 'Fisnida' (unpatented), and 'Volcano' (U.S. Plant Pat. No. 5,940). The male parent of 'Fisromon' was the unpatented hybrid seedling No. 92-175-18, with salmon and white, semi-double flowers, medium green leaves with weak zonation, and moderately vigorous growth habit.

'Fisromon' was selected as one flowering plant within the progeny of the stated cross by Angelika Utecht in 1999 in a controlled environment in Moncarapacho, Portugal.

The first act of asexual reproduction of 'Fisromon' was accomplished when vegetative cuttings were taken from the initial selection in the fall of 1999 in a controlled environment in Moncarapacho, Portugal, by, or under the supervision of, Angelika Utecht.

Horticultural examination of plants grown from cuttings of the plant initiated in May 2000 in Hillscheid, Federal Republic of Germany, and continuing thereafter, has demonstrated that the combination of characteristics as herein disclosed for 'Fisromon' are firmly fixed and are retained through successive generations of asexual reproduction.

'Fisromon' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

BRIEF SUMMARY OF THE INVENTION

The following traits have been repeatedly observed and are determined to be basic characteristics of 'Fisromon' in combination distinguish this geranium as a new and distinct cultivar:

1. Bright salmon-pink flowers with a narrow white margin;
2. Large inflorescences and long, strong peduncles;
3. Deep green foliage with strong zonation;
4. Fairly vigorous growth, medium to tall, semi-spherically shaped plant habit, and
5. Medium spring flowering response.

Of the many commercial cultivars known to the present inventor, the most similar in comparison to 'Fisromon' are the patented varieties 'Fisorange' (U.S. Plant Pat. No. 12,485), 'Fishelen' (U.S. Plant Pat. No. 12,722), and 'Fissalm' (U.S. Plant Pat. No. 12,454).

In comparison to 'Fisorange', 'Fisromon' has somewhat less deep orange colored flowers, and grows distinctly taller. In comparison with 'Fishelen', 'Fisromon' has a somewhat deeper salmon flower color, less distinct white margin, and a much taller plant habit. In comparison with 'Fissalm', inflorescences of 'Fisromon' are higher above the foliage, the leaves are not quite so big, and zonation is somewhat stronger.

BRIEF DESCRIPTION OF THE DRAWING

The accompanying photographic drawing shows typical flower and foliage characteristics of 'Fisromon' with colors being as true as possible with an illustration of this type.

DETAILED BOTANICAL DESCRIPTION

The measurements were taken in Hillscheid, Germany, in mid May 2003, 11 weeks after planting of rooted cuttings. The plants were grown in 14 cm pots, they had not been pinched. In the following description color references are made to The Royal Horticultural Society Colour Chart. The color values were determined indoors from plants growing in a green-house in May 2003 in Hillscheid, Germany.

INFLORESCENCE

Umbel:

*Shape.*—Semi-spherical.

*Average diameter.*—122 mm.

*Average depth.*—60 mm.

*Peduncle length.*—200 mm, diameter 3–4 mm.

*Peduncle color.*—Light green, RHS 143 C, partly brown, from RHS 173 A to 173 B.

*Pedicel.*—36 mm in length.

*Pedicel color.*—Near base light green, RHS 144 B, main part brownish, from RHS 173 A to 173 C.

*Number of flowers per umbel.*—About 50–75.

Corolla:

*Average diameter.*—46 mm.

*Form.*—Semi-double-type.

*Shape.*—Cup-like, with few inner petals, round outline, with the upper petals about the same size as the lower petals.

*Number of petals.*—6–7.

*Shape of petals.*—Obovate, base acute, upper end is truncate or rounded, margin is entire. Size of petals: Upper petals: 21–24 mm long, 18–20 mm wide; lower petals: 21–23 mm long, 20–22 mm wide.

*Number of petaloids.*—Most often 2, narrower in shape than the petals.

*Color (general tonality from a distance of three meters).*—Salmon-orange with a little white.

*Color of upper petals.*—Main part RHS 40 B, near margin light pink, RHS 52 C, to white, RHS 155 D.

*Markings of upper petals.*—Weak pink spot, RHS 52 B, near the base.

*Color of lower petals.*—Mainly RHS 40 B, near margin RHS 56 D or 155 D.

*Markings of lower petals.*—None.

*Color of lower surface of petals.*—Marbled, RHS 43 D, RHS 43 C, 55 C and 155 D.

*Color of sepals.*—Outer surface: light green, RHS 143 B, near base weakly brownish infused, RHS 179 B; inner surface: light green, RHS 143 C, near base RHS 179 B.

*Number of sepals.*—5.

*Shape of sepals.*—Linear to lanceolate, acute tip, truncate base, surface with very weak pubescence, margin entire.

*Size of sepals.*—About 10 mm long, 3–4 mm wide for the largest upper sepal, 3 mm in width for the other sepals.

Bud: (just prior to petals unfolding)

*Shape.*—Elliptical.

*Color of sepals.*—Light green, RHS 143 B.

*Color of petals.*—Marbled, between RHS 40 C and 38 C Length: 15 mm Width: 8 mm.

REPRODUCTIVE ORGANS

*Androecium.*—7 fertile anthers, plenty pollen, yellow-orange, RHS 30 A, filaments white, RHS 155 D, to light-pink, RHS 52 D.

*Gynoecium.*—One pistil, red style, RHS 44 A, stigma 5–6-lobed stigma, red, RHS 44 A.

*Fertility/seed set.*—No seed set observed.

Spring flowering response period: In Hillscheid, Germany, in 2001 plants had on average 0.5 flowers opened 8 weeks after planting of rooted cuttings Outdoor flower production: Continuously and moderately rich flowering the flower count in 2003 in Hillscheid, Germany, indicated about 2 inflorescences per plant in mid May.

Durability: Good stability of flower color, fair rain resistance

Lastingness of the individual flower: About 8 days at 18° C., about 15 days for the umbel Fragrance: None

PLANT

Foliage:

*Shape.*—Kidney-shaped to nearly round, with cordate base, with the gap between the lowest lobes closed or nearly closed, apex rounded with weak lobes.

*Margin.*—Bicrenate.

*Texture.*—Upper surface smooth, dull.

*Size of leaf.*—110 mm wide, 65 mm long.

*Color of upper surface.*—Medium green, closest to RHS 137 C.

*Color of zonation.*—Strong, brown, about RHS 166 A.

*Color of lower surface.*—RHS 137 D.

*Petioles.*—75 mm long, 2–3 mm diameter, green in color, approximately RHS 137 D.

General appearance and form:

*Stem color.*—Mainly green, from RHS 143 A–143 B, in parts weakly infused with brown, RHS 173 A.

*Internode length.*—35–45 mm.

*Branching pattern.*—4–5 branches.

*Size of plants.*—20.0 cm high, 32.3 cm wide (11-week-old plants, as described, measured from the top of the soil (base of the main stem) to the surface of the foliage canopy, without inflorescences).

I claim:

1. A new and distinct cultivar of geranium plant named 'Fisromon', as described and illustrated herein.

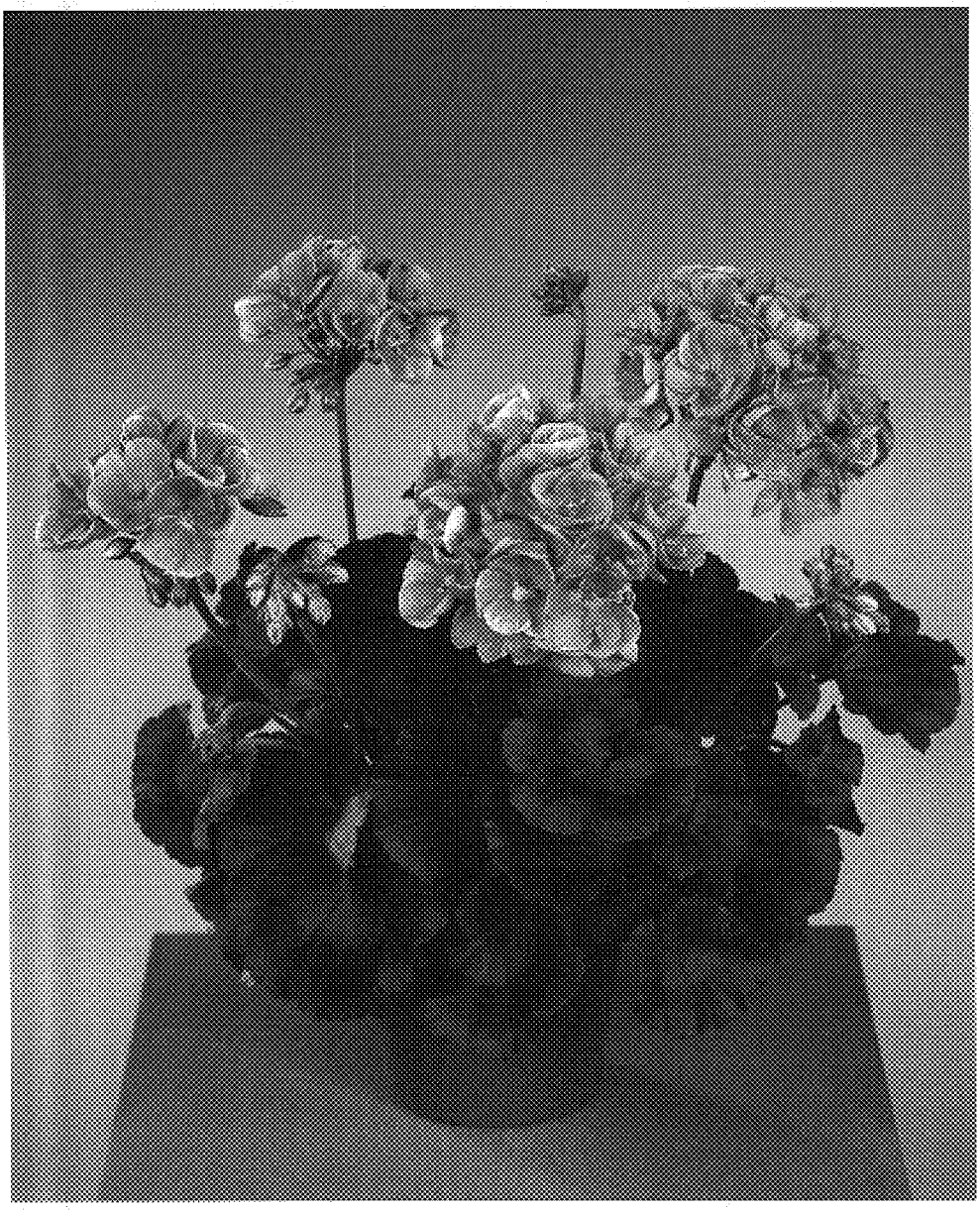

* * * * *